(12) United States Patent
Bernhard et al.

(10) Patent No.: US 8,714,381 B2
(45) Date of Patent: May 6, 2014

(54) CLOSURE DEVICE FOR A REAGENT CONTAINER

(75) Inventors: Joachim Bernhard, Karben (DE); Joerg Filzinger, Kriftel (DE); Hugo Wilmes, Bad Soden (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 0 days.

(21) Appl. No.: 13/215,707

(22) Filed: Aug. 23, 2011

(65) Prior Publication Data

US 2012/0048861 A1    Mar. 1, 2012

(30) Foreign Application Priority Data

Aug. 24, 2010 (DE) .......................... 10 2010 035 219

(51) Int. Cl.
*B65D 17/44* (2006.01)
*B67B 7/00* (2006.01)

(52) U.S. Cl.
CPC ........................ *B67B 7/24* (2013.01)
USPC ........ 215/297; 215/228; 220/278; 220/345.1; 220/212.5

(58) Field of Classification Search
CPC ............................................. B67B 7/24
USPC ......... 220/278, 277, 265, 526, 525, 812, 811, 220/810, 254.8, 254.3, 254.2, 254.1, 254.9, 220/345.4, 345.1, 212.5, 212; 215/297, 215/296, 295, 301, 228, 223; 222/541.8, 222/541.7, 541.6, 541.1, 541.2, 560, 559, 222/561; 81/3.56, 3.57, 3.55, 3.07
IPC ........................................................ B65D 17/44
See application file for complete search history.

(56) References Cited

U.S. PATENT DOCUMENTS

| 905,362 | A | * | 12/1908 | Pratt .............................. 220/291 |
| 4,548,339 | A | * | 10/1985 | Gorman .......................... 222/129 |
| 5,141,133 | A | * | 8/1992 | Ninomiya et al. ............... 222/83 |
| 5,885,529 | A | | 3/1999 | Babson et al. |
| 6,043,097 | A | * | 3/2000 | Dumitrescu et al. ............ 436/48 |

(Continued)

FOREIGN PATENT DOCUMENTS

| EP | 0703457 | 3/1996 |
| EP | 1046915 A2 | 10/2000 |

(Continued)

OTHER PUBLICATIONS

Search Report of European Patent Application No. 11177532.6 mailed on Nov. 17, 2011.

(Continued)

*Primary Examiner* — Robert J Hicks
(74) *Attorney, Agent, or Firm* — King & Spalding L.L.P.

(57) ABSTRACT

A closure device including a first and second closure element, the first closure element, which has an opening, being mounted on the opening of a container to be closed and the second closure element being movably connectable to the first closure element, the first closure element of the device having on the bottom surface facing the container a raised edge, which encircles the opening and has a sharp-edged region and a blunt region.

14 Claims, 6 Drawing Sheets

(56) References Cited

U.S. PATENT DOCUMENTS

| | | | |
|---|---|---|---|
| 6,398,075 B1 * | 6/2002 | Laciacera et al. | 222/91 |
| 6,851,576 B2 * | 2/2005 | Dubach | 222/83 |
| 6,866,820 B1 | 3/2005 | Otto et al. | |
| 7,435,381 B2 | 10/2008 | Pugia et al. | |
| 2003/0132244 A1 * | 7/2003 | Birkmayer et al. | 222/83 |
| 2005/0242113 A1 * | 11/2005 | Weist | 222/83.5 |
| 2006/0071000 A1 * | 4/2006 | Weist et al. | 220/278 |
| 2006/0216210 A1 * | 9/2006 | Dumitrescu et al. | 422/102 |
| 2007/0040009 A1 * | 2/2007 | Sase et al. | 229/125.14 |
| 2009/0020494 A1 * | 1/2009 | Seelhofer | 215/252 |
| 2009/0250488 A1 * | 10/2009 | Dubach | 222/83 |

FOREIGN PATENT DOCUMENTS

| | | |
|---|---|---|
| EP | 1707966 | 10/2006 |
| EP | 1898220 | 3/2008 |
| EP | 1918721 A1 | 5/2008 |
| EP | 2194385 A1 | 6/2010 |
| WO | 2007068094 A1 | 6/2007 |

OTHER PUBLICATIONS

European Search Report of European Patent Application No. EP 11177532 issued on Feb. 14, 2012.

* cited by examiner

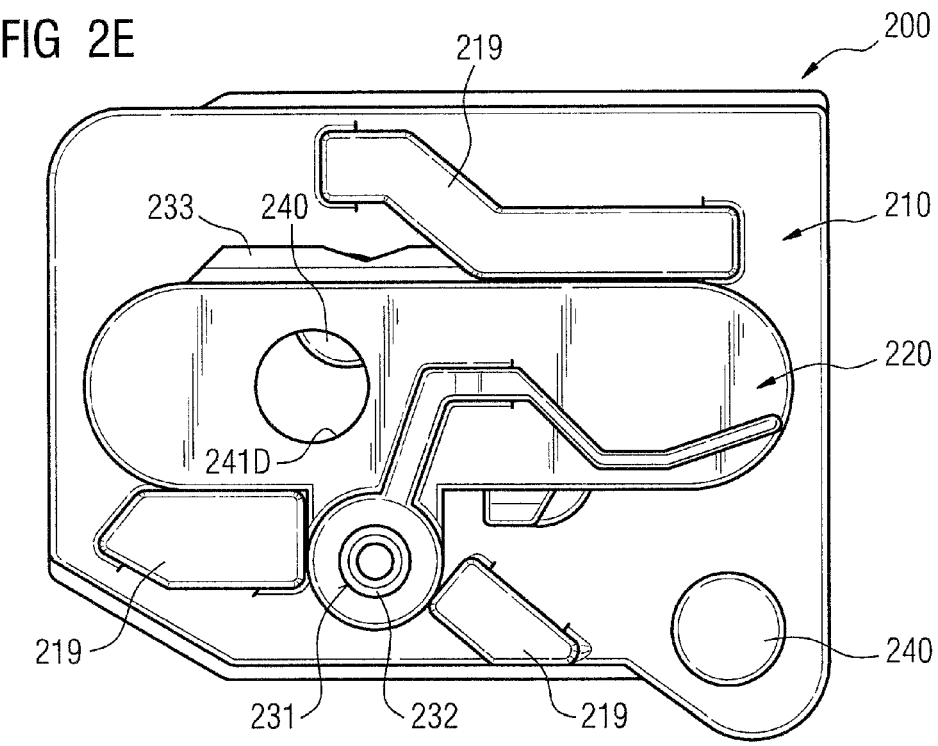
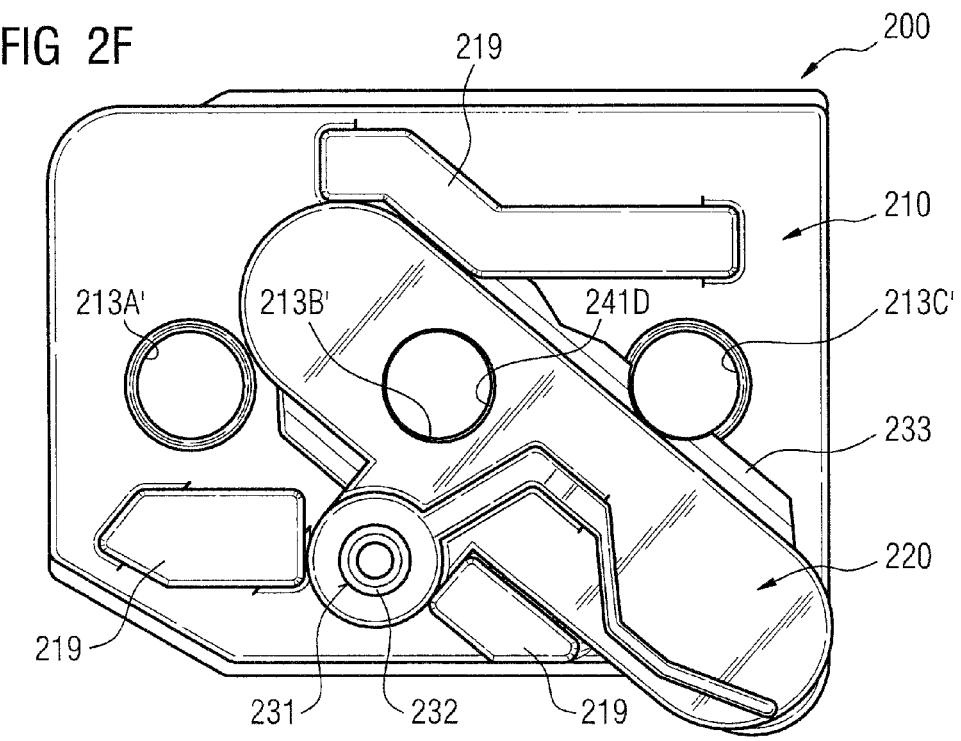

CLOSURE DEVICE FOR A REAGENT CONTAINER

PRIORITY STATEMENT

The present application hereby claims priority under 35 U.S.C. §119 of German Patent Application Number 10 2010 035 219.5 filed Aug. 24, 2010, the entire contents of which are hereby incorporated herein by reference.

FIELD OF INVENTION

The invention relates to a closure device for the closure of reagent containers.

BACKGROUND OF INVENTION

A plurality of devices are used in the area of medical diagnostics fully automatically carrying out the necessary method steps, such as, for example, pipetting, mixing, incubating, centrifuging, measuring etc. The samples that are analyzed by means of such devices are, in the majority of cases, human or animal body fluids or other analyte-containing fluids to which frequently at least one test reagent has to be added. The storage, the removal, the transfer and the addition of fluids, which can be located in the most varied containers, are, therefore, essential operations in the interior of the diagnostic devices.

One criterion to be taken into consideration when setting up tests on partly automatic or fully automatic diagnostic devices is the storage life of the reagents when stored in the device, the so-called on-board stability, which is influenced definitively by the conditions in the device. Particularly problematic are the loss in mass of fluid reagents brought about by evaporation and the risk of contamination. To determine analytes in a standardized and reliable manner, it is essential to use reagents in a defined composition, which means that any changes in concentration, brought about by fluid losses, can impair the quality or the so-called performance of the entire test. The reason why fluid reagents evaporate is that they have to be directly accessible to the automatic pipettors and are, consequently, not as a rule hermetically sealed.

Depending on the design of the devices or pipettors, as is known, different measures are taken to reduce the evaporation of fluids from the reagent containers. For example, many diagnostic devices have cooled holders or positions into which the reagent containers are inserted. By cooling the reagents, the evaporative fluid loss can be reduced in a considerable manner. Another measure for reducing the effects of evaporation is decreasing the cross-sectional opening of the reagent container, which, however, is only able to be adapted to a restricted extent, limited by the dimensions of the pipettor. The use of closure caps or plugs that are more or less hermetically sealed is also customary.

A particularly impermeable protection against evaporation and a particularly efficient protection against contamination is offered by closure devices which seal off the opening of the reagent container as hermetically as possible, such as, for example, screw-type closures or snap-type closures, and which are designed such that they can be automatically opened and closed again by means of a corresponding mechanism in the diagnostic device. However, one disadvantage is that extremely complicated mechanisms and devices have to be installed on the devices for automatically opening and closing such closure devices.

Another closure device which ensures efficient protection against evaporation and contamination is described in EP-A2-1046915. This latter describes a two-part reagent container closure comprising a closure body with an opening which is mounted on the opening of the reagent container. A closure cover, which releases the opening of the reagent container in the open position and closes the opening of the reagent container in the closed position, is movably connectable to the closure body. The opening and closing of the opening of the reagent container is effected by the closure cover being moved in a horizontal plane in relation to the closure body. So that the closure device can be actuated automatically, the closure cover has a so-called entrainment means and the ram of a corresponding arrangement of the device, in which the reagent container is located, is able to cooperate with said entrainment means. The horizontal movement of the closure cover is brought about by a horizontal movement of the ram or of the reagent container and the reagent container is consequently opened or closed.

An additional challenge is connected to the storage of light-sensitive reagents in diagnostic devices. Modern test methods are increasingly based on highly sensitive photochemical methods. The reagents used in this case contain light-sensitive components, such as photo-sensitizers or chemiluminescent or fluorescent substances which are excited by the effect of light. In order to ensure the on-board stability of light-sensitive reagents, any effect of light must be avoided as much as possible. To this end, these types of reagents are usually filled in containers which are produced from a light-tight material, preferably a colored plastics material. The reagent containers are hermetically sealed for the transporting and storing of the reagents until they are positioned in the diagnostic device. The reagent container opening is usually heat-sealed with a light-tight foil by the manufacturer for this purpose.

One disadvantage with these types of foil seals, which are also used, moreover, for the transporting and storing of non-light-sensitive reagents, is that the foil has to be removed by hand from the reagent container by the user before a suitable automatically re-closable closure device can be applied, by means of which the reagent container is then positioned in the diagnostic device. The manual removal of the foil and the resultant handling at the opened reagent container involves the risk of the reagent being shaken or contaminants passing into the container. As the user must, therefore, act particularly carefully in order to avoid the named risks, the removal of foil seals and the ensuing mounting of the closure devices is also an operating step that is expensive in time and consequently cost. One particular disadvantage when removing the foil from reagent containers that contain light-sensitive reagents and then mounting the closure device is that these steps should be carried out, as much as possible, protected from light, i.e. in a dark room. The user's blind handling, however, increases the named risks of shaking and contaminating the container.

SUMMARY OF INVENTION

Consequently, it is the object of the present invention to provide a re-closable closure device for a foil-sealed reagent container, said closure device offering as efficient a protection as possible against evaporation and contamination and making it possible, additionally, for manual removal of any possible foil seal to be dispensed with.

This object is achieved in that there is provided a closure device which comprises a first and second closure element, the first closure element, which has an opening, being mounted on the opening of the container to be closed and the second closure element being movably connectable to the first closure element, the first closure element of the device having on the bottom surface facing the container a raised edge, which encircles the opening and has a sharp-edged region and a blunt region.

The advantage of this is that any possible foil seal of the reagent container opening is penetrated when the closure device is mounted onto a reagent container. The fact that the circumferential edge on the bottom surface of the first closure element also has a blunt, that is to say non sharp-edged, region along with the sharp-edged region for perforating, cutting or penetrating a foil, ensures that the cutout portion is not completely separated from the remaining foil, but only projects into the container and remains connected to the foil. This prevents the foil cutout portion falling into the vessel.

BRIEF DESCRIPTION OF THE DRAWINGS

A more complete appreciation of the present invention and many of the attendant advantages thereof will be readily understood by reference to the following detailed description when taken in conjunction with the accompanying drawings, in which:

FIG. 1 shows schematic representations of one embodiment of the device as claimed in the invention for the light-tight closure of a container with one opening.

FIG. 2 shows schematic representations of an embodiment of the device as claimed in the invention for the light-tight closure of a three-chambered container having three openings.

FIG. 2E shows a top view from above onto a device comprising a first closure element and a second closure element in the closed position.

FIG. 2F shows a top view from above onto a device comprising a first closure element and a second closure element in the open position.

DETAILED DESCRIPTION OF INVENTION

Figure 1A:
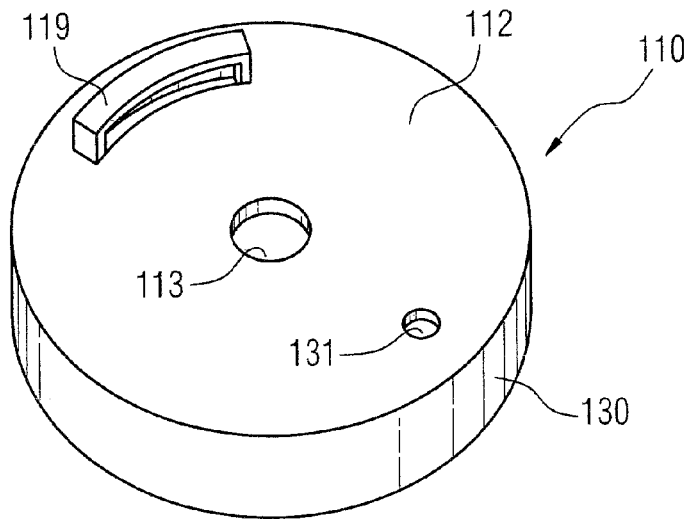
FIG. 1A shows the first closure element of the device in a view from above onto the top surface remote from the container.

The closure device as claimed in the invention is suitable for closing a container which has at least one opening.

One object of the present invention, consequently, is a device for the light-tight closure of a container with one opening, said device having a) a first closure element with a bottom surface facing the container and a top surface remote from the container and with at least one opening, said closure element being shaped such that it is mountable in a form-fitting manner on the container such that the opening of the closure element is situated above the opening of the container, and b) a second closure element with a bottom surface facing the first closure element and a top surface remote from the first closure element, said second closure element being movably connectable to the first closure element and, in a closed position, covering the at least one opening of the first closure element and, in an open position, not covering the at least one opening of the first closure element, and wherein a raised edge, which encircles the at least one opening, is provided on the bottom surface of the first closure element, said edge having a first longitudinal portion with a sharp-edged surface and a second longitudinal portion with a blunt surface.

In a preferred embodiment, the second longitudinal portion of the raised edge, which has a blunt surface, extends in a curved manner on the outer surface, i.e. on the side remote from the opening. The effect of this is that the foil cutout portion is deformed in a curve manner (concave) at the point where it remains connected to the foil. This type of deforming stabilizes or stiffens the foil cutout portion protruding into the container, thereby avoiding any fluttering of the foil cutout portion which could obstruct access through the closure element and the container opening.

The blunt surface of the second longitudinal portion is preferably simply a smooth surface. It can extend in a plane-parallel manner in relation to the bottom surface of the first closure element. As an alternative, the surface can lie in one plane, which is inclined in relation to the bottom surface of the first closure element.

The sharp-edged surface of the first longitudinal portion of the raised edge, which encircles the opening of the first closure element, preferably has tooth-shaped and/or cutting edge-shaped structures. The type of the structure or the type of the arrangement of different structures (cutting edge geometry) for creating a sharp-edged surface on the first longitudinal portion of the raised edge can be optimized depending on the character of the material to be penetrated, by means of which material the container opening is sealed, in order to ensure as easy a penetration as possible.

The first longitudinal portion of the raised edge, which has a sharp-edged surface, preferably projects at least partially beyond the second longitudinal portion of the raised edge, which has a blunt surface, with reference to the height thereof. The advantage of this is that when the first closure element is mounted onto a foil-sealed container, the longitudinal portion with the sharp-edged surface comes into contact first of all with the foil to be penetrated and all the force exerted is exerted onto the sharp-edged region of the circumferential edge. This makes penetration of the material to be penetrated easily possible using a small amount of force. Penetration with a small amount of force can be facilitated additionally in that the first longitudinal portion of the raised edge, which has a sharp-edged surface, slants upwards in an inclined manner or in the shape of a ramp from the bottom surface of the first closure element, that is to say lies in a plane which is inclined in relation to the bottom surface of the first closure element. The angle of inclination of the plane is preferably approximately between 1 and 45°.

In one particular embodiment, the first longitudinal portion of the raised edge, which encircles the opening of the first closure element and has a sharp-edged surface, has a first, a second and a third part portion, wherein the first and the third part portion extend in each case in a straight line and wherein the second part portion, which connects the first and the third part portion together, extends in a curved manner. The first and third part portion can extend parallel to each other or can extend slightly inclinedly to each other such that—if they were lengthened they would intersect outside the circumferential raised edge. The first and/or the third part portion each preferably has a cutting edge which extends over the entire length of the respective part portion. In addition, the second part portion, which connects the first and third part portion together, preferably has tooth-shaped structures. In particular, in conjunction with a ramp-shaped development of the first longitudinal portion of the raised edge, with the maximum height at the summit of the curved second part portion, this embodiment ensures that the material to be penetrated, by means of which material the container opening is sealed, is perforated at one position initially by means of the tooth-shaped structures of the second part portion and, with pressure applied, proceeding from the perforated position, is cut through cleanly by means of the cutting edges of the first and third part portion. Along with controlled penetration of the material to be penetrated using a small amount of force, this ensures that the foil cutout portion has clean cut edges, as a result of which the cut edges are prevented from becoming frayed. Cut edges that become frayed could protrude into the container opening and thus obstruct the access, for example of the pipettors.

The movable connection between the first and second closure element can be produced, for example, by a detachable plug-in connection. To this end, the two closure elements have interlocking structures such as, for example, a pin and a corresponding bore. The movable connection forms a pivotal point. The pivotal point is arranged such that the second closure element is movable in a horizontal plane in relation to the first closure element. The radius of movement is to be selected such that an open position, in which all openings present in the first closure element are accessible, and a closed position, in which all openings present in the first closure element are closed, can be achieved.

A further embodiment of the closure device as claimed in the invention is characterized such that it is suitable for the light-tight closure of a multi-chambered container.

Test kits, which contain different reagents for carrying out a diagnostic method, can be provided, for example, in the form of a multi-chambered reagent container, in which the different reagents are stored separately.

The term "multi-chambered container" includes a container comprising at least two chambers for accommodating and storing fluids. The container can be designed in one piece or can have multiple separate chambers which are interconnected. A multi-chambered container can include three, four, five or more chambers.

For closing a multi-chambered container with at least two openings in a light-tight manner, the closure device, which consists of a first and a second closure element, has in the first closure element, which is mounted on the container to be closed, at least two openings, which, when the closure element is mounted on the container, are located above the openings of the container. A raised edge, which encircles the opening and has a sharp-edged region and a blunt region, is provided for each opening on the bottom surface of the first closure element facing the container.

A further object of the present invention, consequently, is a device for the light-tight closure of a multi-chambered container with at least two openings, said device having a) a first closure element with a bottom surface facing the container and a top surface remote from the container and with at least two openings, said closure element being shaped such that it is mountable in a form-fitting manner on the container such that the openings of the closure element are situated above the openings of the container, and a second closure element with a bottom surface facing the first closure element and a top surface remote from the first closure element, said second closure element being movably connectable to the first closure element and, in a closed position, covering the openings of the first closure element and, in an open position, not covering the openings of the first closure element, and wherein a raised edge, which encircles the opening, is provided on the bottom surface of the first closure element for each opening, said edge having a first longitudinal portion with a sharp-edged surface and a second longitudinal portion with a blunt surface.

The second closure element, which has a bottom surface facing the first closure element and a top surface remote from the first closure element and which is movably connectable to the first closure element, serves for the opening and closing of the one opening or of the multiple openings in the first closure element and consequently the opening and closing of the opening of the container or of the multiple openings of a multi-chambered container. To this end, the second closure element is movable between an open position and a closed position. This brings about optimum protection of the container interior from evaporation and light incidence in the closed state as well as unobstructed access to the chamber(s) in the open state, e.g. for a pipettor.

The second closure element preferably has an entrainment means on the top surface and a horizontal force can act on said entrainment means, as a result of which the second closure element is movable from the closed position into the open position and vice versa. The advantage of this is that the closure device can be opened and re-closed simply by means of a suitable rod-shaped object, which is arranged in a perpendicular manner and is able to exert a horizontal force onto the entrainment means. The horizontal force can be generated either by a movement of the rod-shaped object in relation to the container or by a movement of the container in relation to the rod-shaped object. This embodiment of the closure device is particularly suitable for use in an automatic diagnostic device.

The first closure element, on the top surface remote from the container, preferably has guide bridges for guiding the second closure element, which is movable. This has the effect of establishing the direction of movement or the radius of movement of the second closure element. The second closure element preferably has corresponding winged edges, which interact in such a manner with the guide bridges of the first closure element that in the closed position and in the open position an increased pressing pressure acts on the second closure element. This brings about stabilization of the closed position and of the open position of the second closure element, thereby avoiding unwanted intermediate positions into which the second closure element could be moved as a result of vibrations or other mechanical influences which can occur, in particular, in automatic diagnostic devices.

In each case a sealing lip, that is to say a circumferential, slightly raised edge, is preferably provided on the bottom surface of the second closure element for each opening of the first closure element, said sealing lip being developed in each case such that, in the closed position, it encircles each of the openings in a sealing manner. This has the effect of improving the evaporation protection and increasing the light-tightness of the closure device in the closed position.

An elevation is preferably provided on the top surface of the first closure element for at least one sealing lip, which is present on the bottom surface of the second closure element, said elevation being arranged such that, in the open position of the closure element, it is encircled with accuracy of fit by the sealing lip. It is also possible to provide an elevation for each sealing lip present. As an alternative to or in addition to the above-described stabilization by means of guide bridges and winged edges, the effect of this is to stabilize the open position of the second closure element, thereby avoiding unwanted intermediate positions, into which the second closure element could be moved as a result of vibrations or other mechanical influences.

One particularly preferred embodiment of a closure device as claimed in the invention relates to a device for the light-tight closure of a three-chambered container with three openings (A, B, C), which are arranged in a linear manner. In this embodiment, the first closure element has three openings (A', B', C') which are also arranged in a linear manner. In addition, the second closure element has an opening D, which, in the closed position, is situated between the openings A' and B' and, in the open position, is situated above the opening B' of the first closure element. The advantage of this embodiment is that through the optimum spatial arrangement of the various elements the size of the closure device can be kept relatively small. A small space requirement is desirable in particular for closure devices that are to be used in automatic diagnostic devices as the space is basically very restricted in such devices.

The second closure element in the design, as described for the closure of a container with three openings, can be used, in addition, independently of the first closure element. The second closure element can be used together with a first closure element, it being possible for the latter to have, or not have, on the bottom surface a circumferential edge with a sharp-edged region for perforating, cutting or penetrating a foil. However, the second closure element can also be used without a separate first closure element if the top surface of the container, which has the container openings (A, B, C), is developed such that the second closure element is attachable so as to be movable.

A further object of the present invention, consequently, is a closure element for the light-tight closure of a container with three openings A, B, C, which are arranged in a linear manner. The closure element has a bottom surface facing the container and a top surface remote from the container and is movably connectable to the container. In a closed position, the closure element covers the openings (A, B, C) of the container and, in an open position, does not cover the openings (A, B, C) of the container. The closure element itself has an opening D which, in the closed position, is situated between the openings A and B of the container and, in the open position, is situated above the opening B of the container.

A closure device as claimed in the invention is preferably produced from plastics material, such as, for example, polypropylene, particularly preferred from colored, light-impermeable plastics material. The closure elements of the device as claimed in the invention can be produced, for example, using conventional injection molding technology.

The dimensions of a device as claimed in the invention are to be adapted to the dimensions of the container to be closed.

A device as claimed in the invention is preferably mounted on the container by the first closure element being connected to the container in a positive locking manner. To this end, the first closure element can have an outer wall, which encircles the bottom surface and is developed in a manner that corresponds to the container to be closed such that, by means of pressure, a plug-in connection can be produced with a relatively high level of holding force. A device as claimed in the invention can be mounted by a user manually in this way simply by fitting it together/placing it in position on a container. The height of the outer wall encircling the bottom surface of the first closure element is preferably selected such that it projects beyond the height of the raised edge/edges encircling the opening or openings. The advantage of this is that, when the first closure element or the closure device is mounted on the container, any foil closure is not opened until the outer wall completely surrounds the upper container edge, thereby achieving maximum light-tightness.

The second closure element is either already connected to the first closure element at the time of mounting the first closure element on the container, or it is connected to the same immediately after the first closure element is mounted.

The present invention additionally relates to a test kit for a diagnostic test, said test kit comprising a single-chambered or multi-chambered reagent container, which contains one or more reagents in fluid or dry frozen form and the opening(s) of which is/are hermetically sealed by way of a foil. The test kit as claimed in the invention also comprises a closure device as claimed in the invention which is mounted by the user on the reagent container before the reagent or reagents are used.

The embodiments represented in the figures are to illustrate the present invention and are not to be understood as restrictive.

FIG. 1

FIG. 1 shows schematic representations of one embodiment of the device 100 as claimed in the invention for the light-tight closure of a container with one opening.

FIG. 1A shows the first closure element 110 of the device 100 in a view from above onto the top surface 112 remote from the container. In this example, the first closure element 110 has one opening 113 and one guide bridge 119 for guiding the second closure element 120. The first closure element 110 also has an outer wall 130, which encircles the bottom surface and is developed, in this case, in a circular manner corresponding to the container to be closed such that, by means of pressure, a plug-in connection can be produced with a relatively high level of holding force. In addition, the first closure element 110 has an insertion hole 131, which serves for accommodating a pin 132 (see FIG. 1D), which is mounted on the second closure element 120. The first closure element 110 and the second closure element 120 are movably connectable by means of the plug-in connection.

Figure 1B:
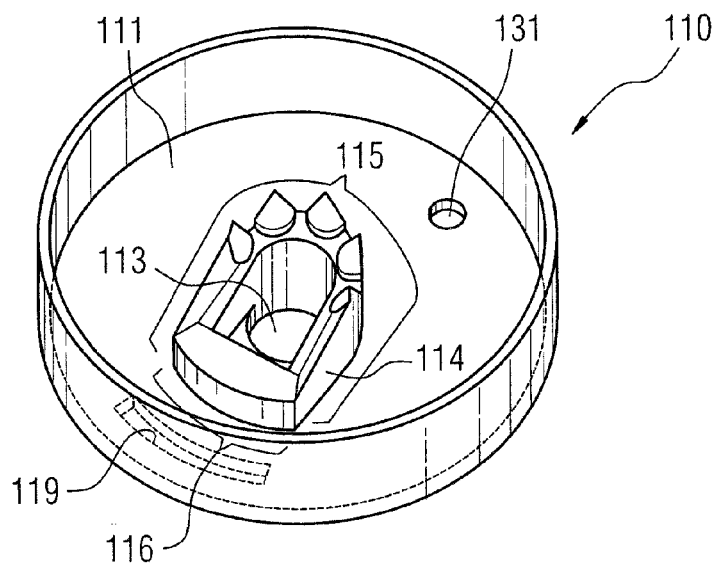
FIG. 1B shows the first closure element of the device in a view from below onto the bottom surface facing the container.

FIG. 1B shows the first closure element 110 of the device 100 in a view from below onto the bottom surface 111 facing the container. A raised edge 114, which encircles the opening 113, is located on the bottom surface 111. The circumferential, raised edge 114 consists of a first longitudinal portion 115 with a sharp-edged surface and a second longitudinal portion 116 with a blunt surface. The outer surface of the second longitudinal portion 116 of the raised edge 114 remote from the opening 113 extends in a curved manner in order to deform the foil cutout portion, which remains connected to the foil in this region, in a curved manner. The foil cutout portion protruding into the container is stabilized or stiffened through this type of deforming, as a result of which the foil cutout portion is prevented from fluttering, which could obstruct access through the closure element and the container opening.

Figure 1C:
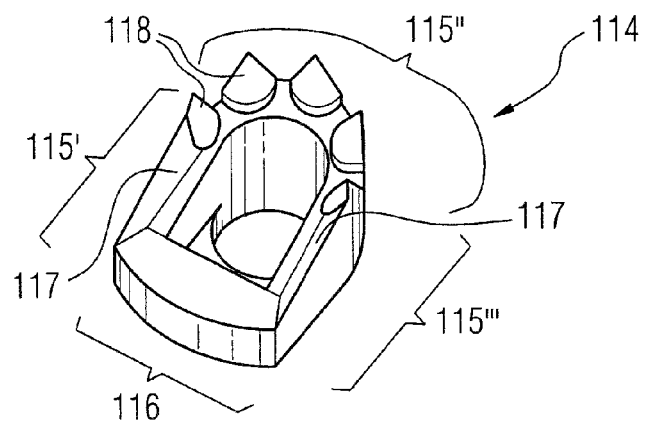
FIG. 1C shows an enlargement of the circumferential, raised edge.

FIG. 1C shows an enlargement of the circumferential, raised edge 114. In this example, the first longitudinal portion 115 of the circumferential, raised edge 114 has both tooth-shaped and cutting edge-shaped structures 118, 117. The first longitudinal portion 115 of the circumferential, raised edge 114, which has a sharp-edged surface, in this case has a first, a second and a third part portion 115', 115" and 115''', the first and the third part portion 115', 115''' extending in each case in a straight line and the second part portion 115", which connects the first and the third part portion together, extending in a curved manner. The first and third part portion extend parallel to each other. The first and the third part portion 115', 115''' have, in each case, a cutting edge 117, which extends over the entire length of the respective part portion. The second part portion 115", which connects the first and third part portion together, has tooth-shaped structures 118.

The first longitudinal portion 115 of the raised edge 114, which has a sharp-edged surface, in this case projects beyond the second longitudinal portion 116 of the raised edge, which has a blunt surface, with reference to the height thereof. The two part portions 115' and 115''' slant in the manner of a ramp and therefore lie in a plane which is inclined in relation to the bottom surface of the first closure element 110. The highest point lies at the summit of the curved part portion 115", which connects the part portions 115' and 115'''. The advantage of this development is that when the first closure element 110 is mounted onto a foil-sealed container, the longitudinal portion with the tooth-shaped, sharp-edged surface comes into contact first of all with the foil to be penetrated and all the force exerted is exerted onto the tooth-shaped region of the circumferential edge 114. This makes possible easy perforation of the material to be penetrated using a small amount of force. As further pressing force is exerted, the cutting edges of the part portions 115' and 115''' cut the foil material, a clean cut edge being created.

Figure 1D:
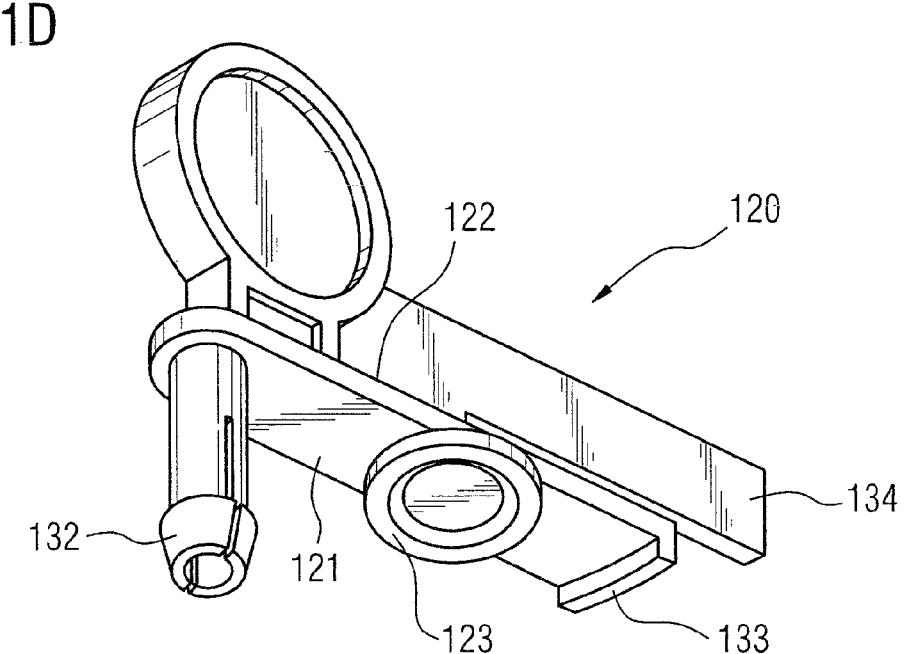
FIG. 1D shows the second closure element of the device in an inclined view from below onto the bottom surface facing the first closure element.

FIG. 1D shows the second closure element 120 of the device 100 in an inclined view from below onto the bottom surface 121 facing the first closure element. The second closure element 120 has a pin 132, which serves for producing the movable connection to the first closure element 110. A sealing lip 123, that is to say a circumferential, slightly raised edge, is provided on the bottom surface 121 of the second closure element 120 for the opening 113 of the first closure element 110 (see FIG. 1A), said sealing lip being developed such that it encircles the opening 113 (see FIG. 1A) in a sealing manner in the closed position. This brings about an improvement in the evaporation protection and an increase in the light-tightness of the closure device in the closed position. The second closure element 120 shown here also has, on the movable end, a winged edge 133 which can engage in the guide bridge 119 of the first closure element 110 (see FIG. 1A), thereby establishing the movement radius of the second closure element 120. In addition, the second closure element 120 shown here also has an entrainment means 134 on the top surface 122 and a horizontal force is able to act on said entrainment means, as a result of which the second closure element 120 is movable from the closed position into the open position and vice versa.

Figure 1E:
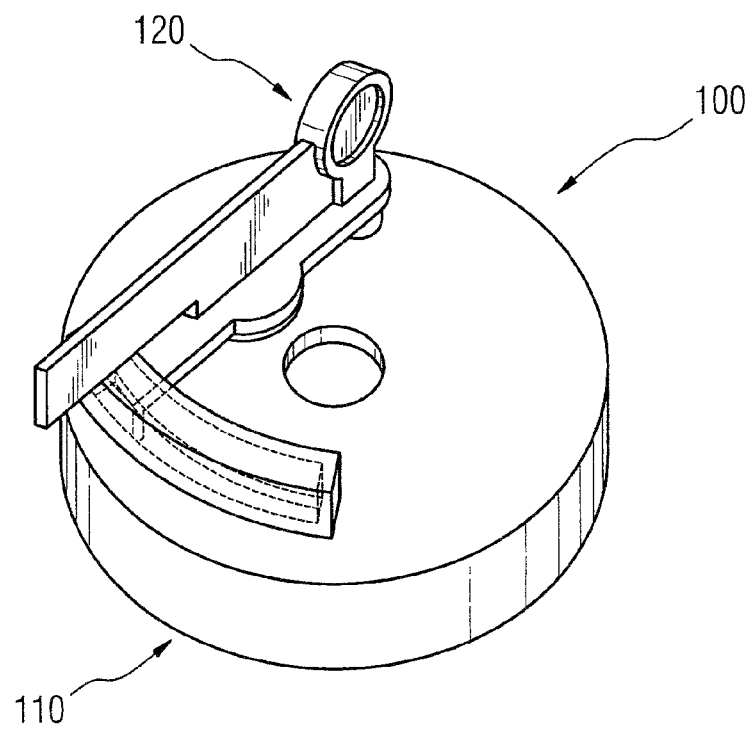
FIG. 1E shows a device comprising a first closure element and a second closure element in the open position.

FIG. 1E shows a device 100 comprising a first closure element 110 and a second closure element 120 in the open position. Access to the interior of the container is possible in this position.
FIG. 2

FIG. 2 shows schematic representations of an embodiment of the device 200 as claimed in the invention for the light-tight closure of a three-chambered container having three openings.

Figure 2A:
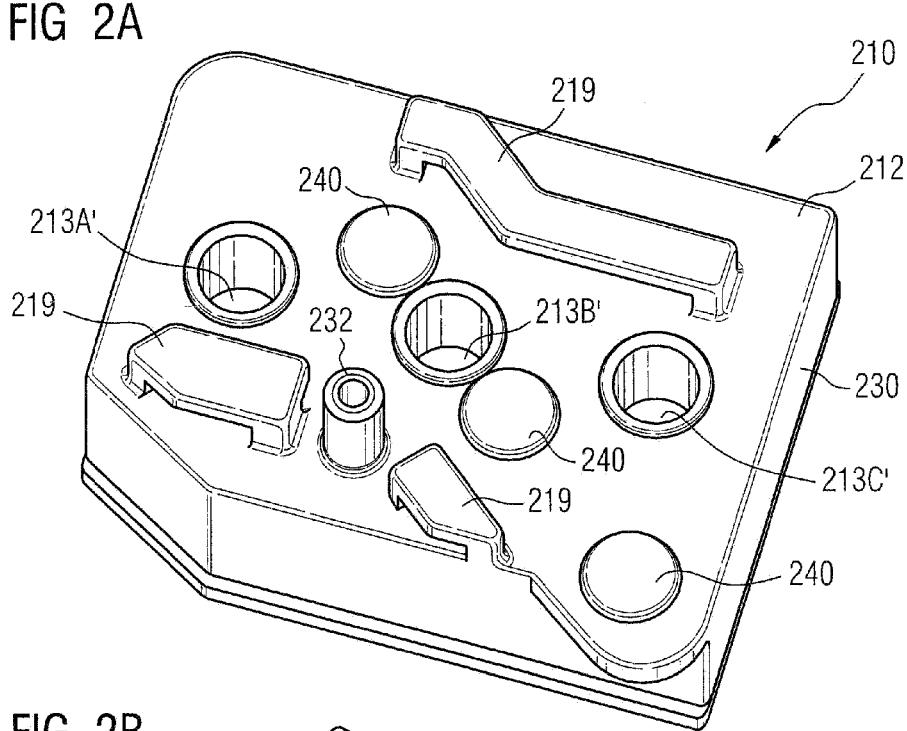
FIG. 2A shows the first closure element of the device in a view from above onto the top surface remote from the container.

FIG. 2A shows the first closure element 210 of the device 200 in a view from above onto the top surface 212 remote from the container. In this example, the first closure element 210 has three openings 213 (A', B', C') and guide bridges 219 for guiding the second closure element 220. The first closure element 210 also has an outer wall 230, which encircles the bottom surface and is developed, in this case, in a rectangular manner corresponding to the container to be closed, such that, by means of pressure, a plug-in connection is producible with a relatively high level of holding force. In addition, the first closure element 210 has a pin 232 for producing the movable connection to the second closure element 220, which has a bore for the accommodation of the pin (see FIG. 2C). The first closure element 210 and the second closure element 220 are movably connectable by means of the plug-in connection. In addition, the closure element 210 shown in this case has three elevations 240 which are arranged such that, in the open position of the closure element 220, they are encircled with accuracy of fit by the sealing lips 223 on the bottom surface of the second closure element 220 (see FIG. 2C). This brings about stabilization of the open position of the second closure element 220, thereby avoiding unwanted intermediate positions into which the second closure element 220 could be moved as a result of vibrations or other mechanical influences.

Figure 2B:
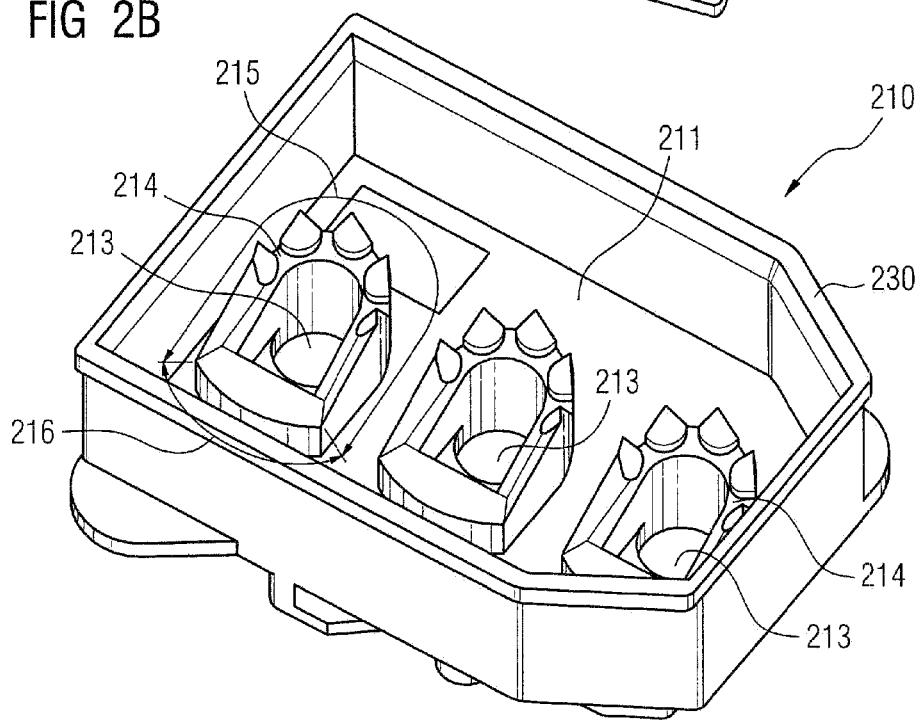
FIG. 2B shows the first closure element of the device in a view from below onto the bottom surface facing the container.

FIG. 2B shows the first closure element 210 of the device 200 in a view from below onto the bottom surface 211 facing the container. A raised edge 214, encircling the opening 213, is situated on the bottom surface 211 for each opening 213. The circumferential, raised edge 214 consists, as already explained in FIGS. 1B and 1C, of a first longitudinal portion 215 with a sharp-edged surface and a second longitudinal portion 216 with a blunt surface. The outer surface of the second longitudinal portion 216 of the raised edge 214 remote from the opening 213 extends in a curved manner in order to deform the foil cutout portion, which remains connected to the foil in this region, in a curved manner.

Figure 2C:
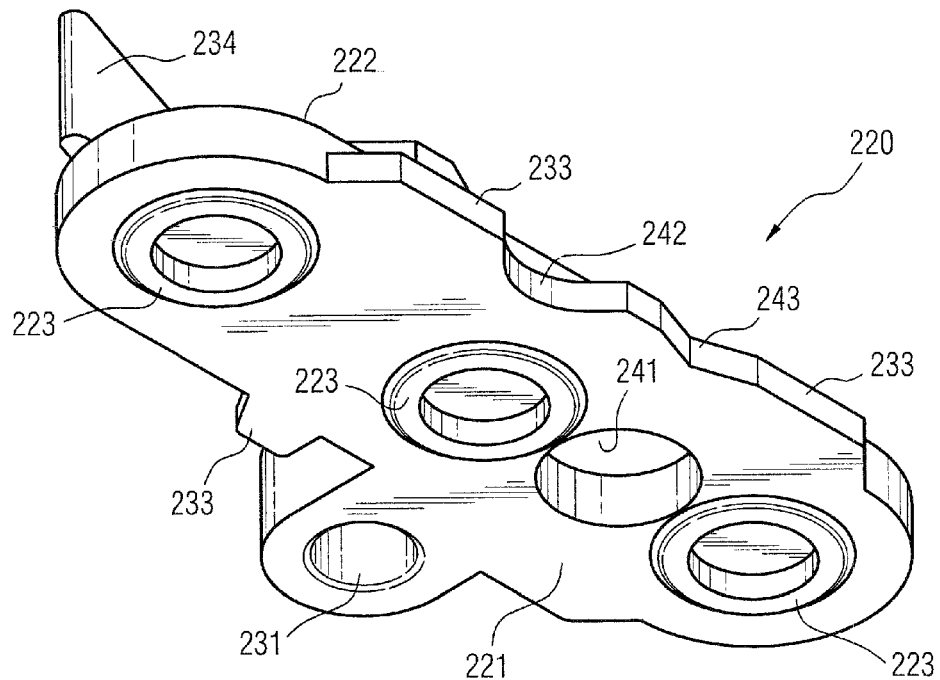
FIG. 2C shows the second closure element of the device in an inclined view from below onto the bottom surface facing the first closure element.

FIG. 2C shows the second closure element 220 of the device 200 in an inclined view from below onto the bottom surface 221 facing the first closure element. The second closure element 220 has an insertion hole 231, for accommodating a pin 232 of the first closure element 210 (see FIG. 2A) and producing the movable connection to the first closure element 210. A sealing lip 223, that is to say a circumferential, slightly raised edge, is provided on the bottom surface 221 of the second closure element 220 in each case for each of the three openings 213 of the first closure element 210 (see FIG. 2A), said sealing lips being developed such that, in the closed position, they encircle the openings 231 in a sealing manner. This has the effect of improving the evaporation protection and increasing the light-tightness of the closure device in the closed position. The second closure element 220 shown here also has winged edges 233, which can engage in the guide bridges 219 of the first closure element 210 (see FIG. 2A), thereby establishing the movement radius of the second closure element 220. In addition, the second closure element 220 shown here has an entrainment means 234 on the top surface 222 and a horizontal force is able to act on said entrainment means, as a result of which the second closure element 220 is movable from the closed position into the open position and vice versa. The example of a second closure element 220 shown in this case also has an opening 241 (D), which is located between the openings 213 A' and 213 B' in the closed position and is located above the opening 213 B' of the first closure element in the open position (see also FIGS. 2E and 2F).

Figure 2D:
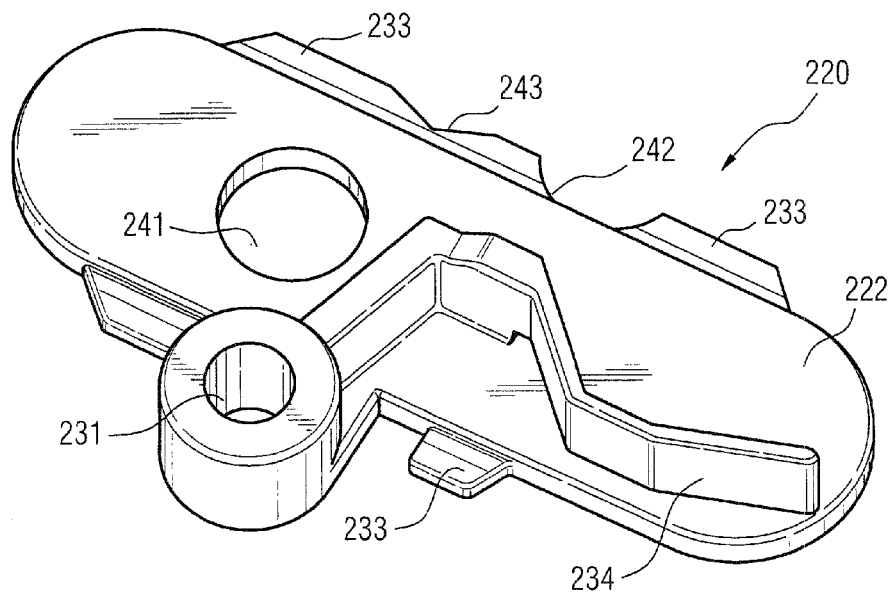
FIG. 2D shows the second closure element of the device in an inclined view from above onto the top surface remote from the first closure element.

FIG. 2D shows the second closure element 220 of the device 200 in an inclined view from above onto the top surface 222 remote from the first closure element. The second closure element 220 has an insertion hole 231, for accommodating the pin 232 of the first closure element 210 and producing the movable connection to the first closure element 210. The second closure element 220 shown here also has specially developed winged edges 233, which can engage in the guide bridges 219 of the first closure element 210, thereby establishing the movement radius of the second closure element 220. The winged edges 233 have recesses at different points. The circular recess 242 is necessary so that, in the open position, the opening 213 C' of the first closure element 210 is not covered partially by the winged edge, consequently obstructing access to the interior of the container (see FIG. 2F). The wedge-shaped recess 243 is necessary so that the closure element 220 can be connected to the closure element 210 or separated from it without the guide bridges 219 and winged edges 233 obstructing each other when they are assembled. To this end, the second closure element 220 has to be moved into a position which lies between the open and closed position. In addition, the second closure element 220 shown here also has an entrainment means 234 on the top surface 222 and a horizontal force can act on said entrainment means, as a result of which the second closure element 220 is movable from the closed position into the open position and vice versa. The example of a second closure element 220 shown here also has an opening 241 (D), which is located between the openings 213 (A') and 213 (B') in the closed position and is located above the opening 213 (B') of the first closure element in the closed position (see also FIGS. 2E and 2F).

FIG. 2E shows a top view from above onto a device 200 comprising a first closure element 210 and a second closure element 220 in the closed position. The interior of all three chambers of the container is protected from evaporation, contamination and light incidence in this position.

FIG. 2F shows a top view from above onto a device 200 comprising a first closure element 210 and a second closure element 220 in the open position. The opening 241 (D) of the second closure element 220 is situated above the opening 213 (B') of the first closure element in this position. Access to all three chambers of the container is possible in this position.

FIG. 3

Figure 3:
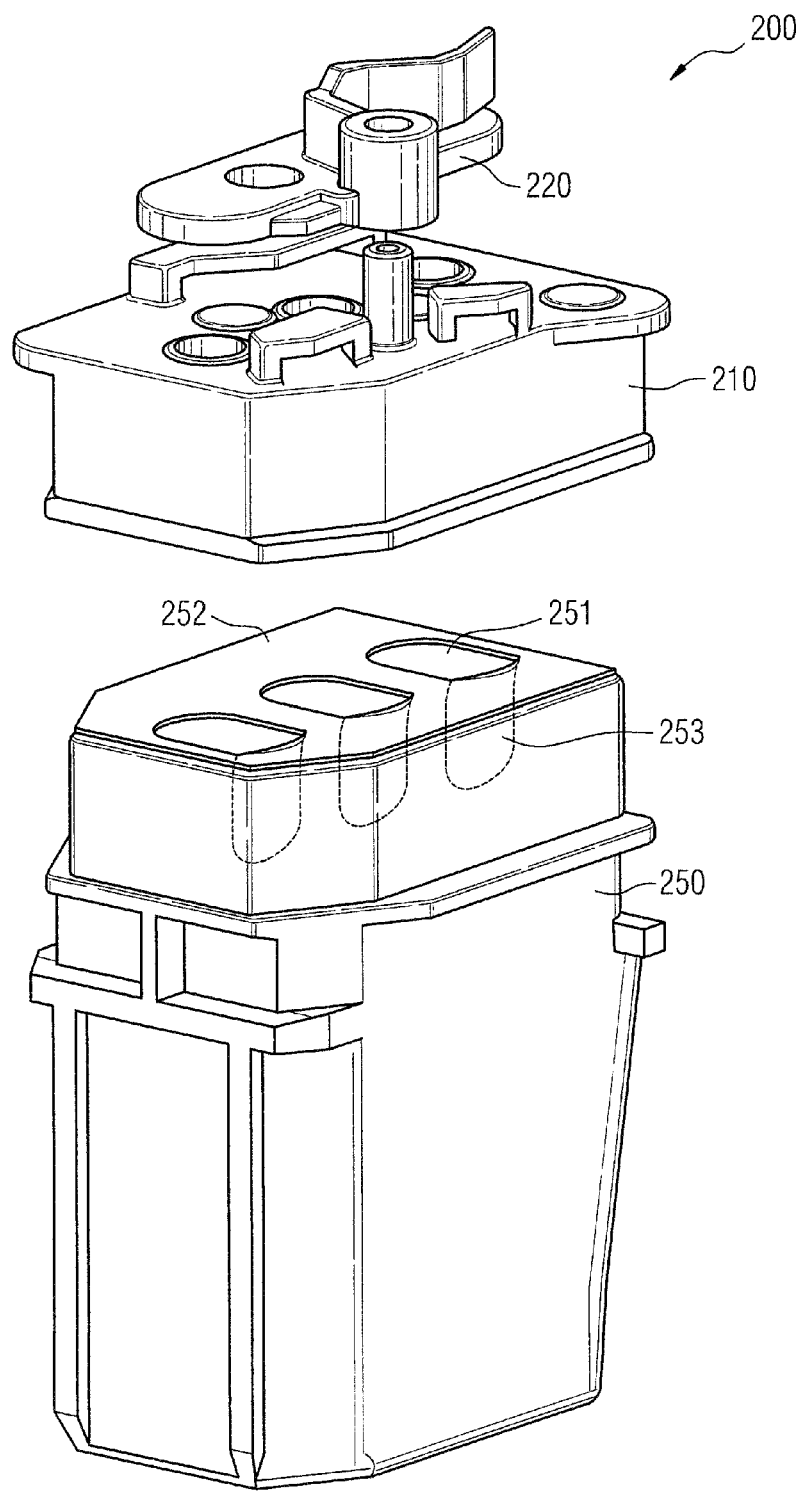
FIG. 3 shows a lateral view of an exploded arrangement of a closure device as claimed in the invention.

FIG. 3 shows a lateral view of an exploded arrangement of a closure device 200 as claimed in the invention, said closure device comprising a first closure element 210 and a second closure element 220 on a three-chambered reagent container 250. The two upright partition walls which divide the interior of the container into three separate chambers are not shown. A foil 252, which covers all three chambers of the container, is mounted on the top surface of the reagent container 251. The arrangement of the closure device 200 on the reagent container 250, which is sealed by way of the foil 252, has cut an opening 251 per container chamber into the foil. The foil cutout portions 253 project into the interior of the container. The fact that they are deformed in a lightly concave manner imparts sufficient rigidity, as a result of which the cutout portions are prevented from fluttering, which could obstruct access into the container opening.

LIST OF REFERENCES

Closure device 100, 200
First closure element 110, 210
Bottom surface of first closure element 111, 211
Top surface of first closure element 112, 212
Opening of first closure element 113, 213
Circumferential, raised edge 114, 214
First longitudinal portion with sharp-edged surface 115, 215
Part portions of first longitudinal portion 115', 115", 115'"
Second longitudinal portion with blunt surface 116, 216
Cutting edge 117
Tooth-shaped structure 118
Guide bridge 119, 219
Second closure element 120, 220
Bottom surface of second closure element 121, 221
Top surface of second closure element 122, 222
Sealing lip 123, 223
Outer wall 130, 230
Insertion hole 131, 231
Pin 132, 232
Winged edge 133, 233
Entrainment means 134, 234
Elevation 240
Opening of second closure element 241
Recess 242, 243
Reagent container 250
Opening of reagent container 251
Foil 252
Foil cutout portion 253

The invention claimed is:

1. A device for the light-tight closure of a container with at least one opening, said device comprising:
   a first closure element with a bottom surface configured to face the container and a top surface configured to be remote from the container and with at least one opening, said closure element being shaped such that it is mountable in a form-fitting manner on the container such that the at least one opening of the closure element is situated above the at least one opening of the container, and
   a second closure element with a bottom surface facing the first closure element and a top surface remote from the first closure element, said second closure element being movably connectable to the first closure element and, in a closed position, covering the at least one opening of the first closure element and, in an open position, not covering the at least one opening of the first closure element, and
   wherein a raised edge, which encircles the at least one opening, is provided on the bottom surface of the first closure element, said edge having a first longitudinal portion with a sharp-edged surface and a second longitudinal portion with a blunt surface;
   wherein the first longitudinal portion of the raised edge has a first, a second and a third part portion, wherein the first and the third part portion each extend in a straight line and wherein the second part portion, which connects the first and the third part portion, extends in a curved manner;
   wherein on the surface of the first or of the third part portion, a cutting edge extends over the entire length of the part portion and wherein the second part portion has tooth-shaped structures;
   wherein the second closure element is moveable relative to the first closure element via a pin and insertion hole arrangement, the pin and insertion hole arrangement offset from the at least one opening and defining a movement radius between the open position and the closed position.

2. The device as claimed in claim 1, wherein at least the outer surface of the second longitudinal portion of the raised edge remote from the opening extends in a curved manner.

3. The device as claimed in claim 1, wherein the sharp-edged surface of the first longitudinal portion of the raised edge has tooth-shaped or cutting edge-shaped structures.

4. The device as claimed in claim 1, wherein a height of the first longitudinal portion of the raised edge is, at least in part, greater than the height of the second longitudinal portion of the raised edge.

5. The device as claimed in claim 1, wherein the first longitudinal portion of the raised edge lies in one plane, which is inclined in relation to the bottom surface of the first closure element.

6. The device as claimed in claim 5, wherein the plane has an angle of inclination of between 1 and 45°.

7. A device for the light-tight closure of a multi-chambered container with at least two openings, said device comprising:
  a first closure element with a bottom surface configured to face the multi-chambered container and a top surface configured to be remote from the multi-chambered container and with at least two openings which are shaped such that said first closure element is mountable in a form-fitting manner on the multi-chambered container such that the openings of the closure element are situated above the openings of the multi-chambered container, and
  a second closure element with a bottom surface facing the first closure element and a top surface remote from the first closure element, said second closure element being movably connectable to the first closure element and, in a closed position, covering the openings of the first closure element and, in an open position, not covering the openings of the first closure element, and
  wherein a raised edge is provided on the bottom surface of the first closure element for each opening, encircling each opening, said edge having a first longitudinal portion with a sharp-edged surface and a second longitudinal portion with a blunt surface;
  wherein the first longitudinal portion of the raised edge has a first, a second and a third part portion, wherein the first and the third part portion each extend in a straight line and wherein the second part portion, which connects the first and the third part portion, extends in a curved manner;
  wherein on the surface of the first or of the third part portion, a cutting edge extends over the entire length of the part portion and wherein the second part portion has tooth-shaped structures;
  wherein the second closure element is moveable relative to the first closure element via a pin and insertion hole arrangement, the pin and insertion hole arrangement offset from the at least one opening and defining a movement radius between the open position and the closed position.

8. The device as claimed in claim 7 for the light-tight closure of a three-chambered container with an opening (A), an opening (B), and an opening (C) which are arranged in a linear manner, wherein the first closure element has an opening (A'), an opening (B'), an opening (C') which are arranged in a linear manner, and wherein the second closure element has an opening (D) which, in the closed position, is situated between the opening (A') and the opening (B') and, in the open position, is situated above the opening (B') of the first closure element.

9. The device as claimed in claim 7, wherein the second closure element has an entrainment means on the top surface and a horizontal force is able to act on said entrainment means, as a result of which the second closure element is movable from the closed position into the open position and vice versa.

10. The device as claimed in claim 7, wherein guide bridges for guiding the second closure element are provided on the top surface of the first closure element remote from the container.

11. The device as claimed in claim 10, wherein the second closure element has winged edges which can interact in such a manner with the guide bridges of the first closure element that in the closed position and in the open position an increased pressing pressure acts on the second closure element.

12. The device as claimed in claim 10, wherein a sealing lip is provided on the bottom surface of the second closure element for each opening, said sealing lip being developed such that, in the closed position, the sealing lip encircles the opening in a sealing manner.

13. The device as claimed in claim 12, wherein an elevation is provided on the top surface of the first closure element for at least one sealing lip, which is present on the bottom surface of the second closure element, said elevation being arranged such that, in the open position, the elevation is encircled with accuracy of fit by the sealing lip.

14. A test kit for a diagnostic test, said test kit comprising:
  a reagent container, at least one opening of which is closed by a foil, and
  a closure device including:
    a first closure element with a bottom surface configured to face the reagent container and a top surface configured to be remote from the reagent container and with at least one opening, said closure element being shaped such that it is mountable in a form-fitting manner on the reagent container such that the at least one opening of the closure element is situated above the at least one opening of the reagent container, and
    a second closure element with a bottom surface facing the first closure element and a top surface remote from the first closure element, said second closure element being movable connectable to the first closure element and, in a closed position, covering the at least one opening of the first closure element and, in an open position, not covering the at least one opening of the first closure element, and
  wherein at least one raised edge, which encircles a corresponding at least one opening, is provided on the bottom surface of the first closure element, said at least one raised edge having a first longitudinal portion with a sharp-edged surface and a second longitudinal portion with a blunt surface;
  wherein the first longitudinal portion of the raised edge has a first, a second and a third part portion, wherein the first and the third part portion each extend in a straight line and wherein the second part portion, which connects the first and the third part portion, extends in a curved manner;
  wherein on the surface of the first or of the third part portion, a cutting edge extends over the entire length of the part portion and wherein the second part portion has tooth-shaped structures;
  wherein the second closure element is moveable relative the first closure element via a pin and insertion hole arrangement, the pin and insertion hole arrangement offset from the at least one opening and defining a movement radius between the open position and the closed position.

* * * * *